United States Patent [19]

Wunder et al.

[11] Patent Number: 5,225,388
[45] Date of Patent: Jul. 6, 1993

[54] METHOD FOR MAKING A CATALYST

[75] Inventors: Friedrich Wunder, Flörsheim am Main; Peter Wirtz, Königstein/Taunus; Günter Roscher, Kelkheim/Taunus; Klaus Eichler, Eschborn, all of Fed. Rep. of Germany

[73] Assignee: Hoechst Aktiengesellschaft, Frankfurt am Main, Fed. Rep. of Germany

[21] Appl. No.: 808,443

[22] Filed: Dec. 16, 1991

Related U.S. Application Data

[62] Division of Ser. No. 621,589, Dec. 3, 1990, abandoned.

Foreign Application Priority Data

Dec. 5, 1989 [DE] Fed. Rep. of Germany ....... 3940125

[51] Int. Cl.⁵ .............................................. B01J 31/04
[52] U.S. Cl. .................... 502/170; 502/243; 502/527
[58] Field of Search ................... 502/170, 527, 243

[56] References Cited

U.S. PATENT DOCUMENTS

| | | | |
|---|---|---|---|
| 3,939,199 | 2/1976 | Farrar et al. | 260/469 |
| 4,093,559 | 6/1978 | Fernholz et al. | 502/170 |
| 4,370,261 | 1/1983 | Wunder et al. | 502/527 X |
| 4,370,492 | 1/1983 | Wunder et al. | 560/245 |
| 4,902,823 | 2/1990 | Wunder et al. | 560/245 |

FOREIGN PATENT DOCUMENTS 2745174 4/1979 Fed. Rep. of Germany.

*Primary Examiner*—Patrick P. Garvin
*Attorney, Agent, or Firm*—Connolly and Hutz

[57] ABSTRACT

The invention relates to a method for making a catalyst which contains palladium and/or its compounds and, if desired, additionally gold and/or gold compounds and which contains as activators alkali metal compounds and, if desired, additionally cadmium compounds on a support which is composed of $SiO_2$ or an $SiO_2$-$Al_2O_3$ mixture having a surface area of 50-250 $m^2/g$ and a pore volume of 0.4-1.2 ml/g and whose particles have a particle size of 4 to 9 mm, 5 to 20% of the pore volume of the support being formed of pores having radii of 200 to 3000 Å and 50 to 90% of the pore volume being formed of pores having radii of 70 to 100 Å. The support particles are compressed with the aid of an Li, Mg, Al, Zn or Mn salt of a $C_2$-$C_{20}$ carboxylic acid or a mixture of such salts as binder.

20 Claims, No Drawings

METHOD FOR MAKING A CATALYST

This application is a division of Ser. No. 621,589, filed Dec. 3, 1990, and now abandoned.

DESCRIPTION

It is known that ethylene can be reacted in the gas phase with acetic acid and oxygen or oxygen-containing gases on solid bed catalysts to give vinyl acetate. Suitable catalysts contain a noble metal component and an activator component. The noble metal component is preferably composed of palladium and/or its compounds; gold and/or its compounds can additionally also be present (U.S. Pat. No. 3,939,199, DE-OS 2,100,778, U.S. Pat. No. 4,668,819). The activator component is composed in this case of compounds of elements of the 1st main group and/or the 2nd main group and/or cadmium. Potassium is preferred as an element of the 1st main group. These active components are applied to supports in finely divided form, silica or alumina in general being used as support material.

The specific surface area of the supports is in general 40–350 $m^2/g$. According to U.S. Pat. No. 3,939,199, the total pore volume should be 0.4–1.2 ml/g, and of this less than 10% should be formed of "micropores" having a pore diameter below 30 Å (Å=angstrom=$10^{-8}$ cm). Suitable supports having these properties are, for example, aerogenic $SiO_2$ or an aerogenic $SiO_2$-$Al_2O_3$ mixture. The support particles in the vinyl acetate preparation in general have the form of spheres. However, tablets and cylinders have also already been employed.

The still unpublished German Patent Application P 39 19 524.4 describes a support which is composed of $SiO_2$ or an $SiO_2$-$Al_2O_3$ mixture having a surface area of 50–250 $m^2/g$ and a pore volume of 0.414 1.2 ml/g and whose particles have a particle size of 4 to 9 mm, 5 to 20% of the pore volume of the support being formed of pores having radii of 200 to 3000 Å and 50 to 90% of the pore volume being formed of pores having radii of 70 to 100 Å.

It has now been fond that it is very advantageous if the support particles are compressed with the aid of carboxylates of Li, Mg, Al, Zn or Mn as binders.

The invention relates to a process for the preparation of vinyl acetate in the gas phase from ethylene, acetic acid and oxygen or oxygen-containing gases on a catalyst which contains palladium and/or its compounds and, if desired, additionally gold and/or gold compounds and also alkali metal compounds as activators and, if desired, additionally cadmium compounds on a support which is composed of $SiO_2$ or an $SiO_2$-$Al_2O_3$ mixture having a surface area of 50–250 $m^2/g$ and a pore volume of 0.4–1.2 ml/g and whose particles have a particle size of 4 to 9 mm, 5 to 20% of the pore volume of the support being formed of pores having radii of 200 to 3000 Å and 50 to 90% of the pore volume being formed of pores having radii of 70 to 100 Å, which comprises compressing the support particles with the aid of an Li, Mg, Al, Zn or Mn salt of a $C_2$-$C_{20}$ carboxylic acid or a mixture of such salts as binder.

The carboxylate or carboxylates are employed in amounts such that the sum of the amounts of Li, Mg, Al, Zn and Mn, calculated as elements, is 0.1 to 5% by weight, based on the support material, preferably 0.3 to 1.5% by weight.

Al carboxylates or Mg carboxylates, in particular Mg carboxylates, are preferably employed. The carboxylic acids preferably have 12 to 18 carbon atoms. The support particles according to the claims can be prepared, for example, as follows: glass microspheres are initially prepared, for example by flame hydrolysis of silicon tetrachloride or a silicon tetrachloride/aluminum trichloride mixture in an oxyhydrogen flame (U.S. Pat. No. 3,939,199). The microspheres can also be prepared by melting very fine $SiO_2$ dust in a sufficiently hot flame and then cooling rapidly. The microspheres prepared in one of the two ways have a surface area of 100–300 $m^2/g$. Microspheres having a surface area of 150–250 $m^2/g$, which are composed of at least 95% by weight of $SiO_2$ and at most 5% by weight of $Al_2O_3$, in particular of at least 99% by weight of $SiO_2$ and at most 1% by weight of $Al_2O_3$, are particularly suitable. Microspheres having said surface area are available commercially, for example under the name ®Aerosil or ®Cabosil or as "highly disperse silicic acid".

Support particles are then pressed from the microspheres with the addition of one or more carboxylates of Li, Mg, Al, Zn or Mn and with the addition of organic fillers (such as sugar, urea, higher fatty acids, long-chain paraffins, microcrystalline cellulose) and lubricants (such as kaolin, graphite, metal soaps), for example by tableting (after precompression) or extruding. The support particles are then calcined in $O_2$-containing gases. When using the Li, Mg, Al, Zn or Mn salts of higher carboxylic acids ($C_{16}$-$C_{20}$) these "soaps" simultaneously act in the tableting as lubricants, so that a separate lubricant does not have to be added. The surface area of the finished support, its pore volume and the proportion of the pore volume which pores of a certain radius form ("pore radii distribution") is determined by the type of shaping (tablets, extrudate pressings etc.), the temperature and duration of calcining, the relative amounts of fillers, lubricants and microspheres and the surface area of the microspheres. Which are the most suitable values for these determining parameters can be determined by simple preliminary experiments.

The finished support obtained by this method has a surface area of 50 to 250 $m^2/g$ and a pore volume of 0.4 to 1.2 ml/g and a particle size of 4 to 9 mm (adjustable by tableting or extruding support particles of suitable size).

By using the supports according to the claims, it is possible to increase substantially the space-time yield of the catalysts compared to conventional supports with otherwise identical conditions (the same content of active substances on the support and the same reaction conditions) and at the same time to lower the most severe side reaction, the combustion of the ethylene to give $Co_2$, by 75%. The ethyl acetate formation occurring as a further side reaction is also distinctly reduced. As a result of this increase in the selectivity from about 92% to about 97%, substantial savings can be achieved and additionally as a result of the increasing efficiency, together with distinctly increased selectivity, the amount of catalyst and reactor volume can be reduced in new plants, which leads to considerable reductions in the plant costs, or the capacity can be significantly increased without alterations in already existing plants, so that the investment costs for the plant expansion are saved.

The surface area of said supports is always the so-called BET surface area, measured by the method of Brunauer, Emmett and Teller. It indicates the total surface area of 1 g of support material, i.e. the sum of the external surface area of the support and of the internal surface area of all open pores. The total pore volume and the proportion thereof which pores of a certain size (for example those having a diameter of 70 to 100 Å) contribute can be measured with the aid of mercury porosimetry. Suitable measuring apparatuses are manufactured, for example, by the firms Carlo Erba or Micromeritics.

The catalytically active substances are applied to the support in a customary manner, for example by impregnating the support with a solution of the active substances, then drying and, if appropriate, reducing. However, the active substances can also be applied, for example, by depositing on the support, by spraying on, evaporating on or immersing.

Suitable solvents for the catalytically active substances are in particular unsubstituted carboxylic acids having 2 to 10 carbon atoms in the molecule, such as acetic acid, propionic acid, n- and iso-butyric acid and the various valeric acids. Owing to their physical properties and also for economic reasons, acetic acid is preferably employed as the solvent. The additional use of an inert solvent is expedient if the substances are insufficiently soluble in the carboxylic acid. Thus, for example, palladium chloride can be dissolved substantially better in an aqueous acetic acid than in glacial acetic acid. Possible additional solvents are those which are inert and miscible with the carboxylic acid. In addition to water, those which may be mentioned are, for example, ketones such as acetone and acetylacetone, in addition ethers such as tetrahydrofuran or dioxane, but also hydrocarbons such as benzene.

The catalyst contains palladium and/or its compounds as the noble metal component and alkali metal compounds as the activator component. It can contain gold and/or its compounds as an additional noble metal component, and it can contain cadmium compounds as an additional activator component.

Possible compounds of palladium are all the salts and complexes which are soluble (and, if appropriate, reducible) and which leave behind no deactivating substances such as halogen or sulfur in the finished catalyst. Particularly suitable compounds are the carboxylates, preferably the salts of aliphatic monocarboxylic acids having 1 to 5 carbon atoms, for example the acetate, the propionate or the butyrate. In addition, for example, the nitrate, nitrite, hydrated oxide, oxalate, acetylacetonate or the acetoacetate are suitable. However, compounds such as the sulfate and the halides can also be used if care is taken that the sulfate radical is removed, for example by precipitating with barium acetate, or the halogen is removed, for example by precipitating with silver nitrate, before impregnation so that the sulfate or halogen anion does not get onto the support. Owing to its solubility and its availability, palladium acetate is the particularly preferred palladium compound.

In general, the content of palladium in the catalyst is 1.0 to 3% by weight, preferably 1.5 to 2.5% by weight, in particular 2 to 2.5% by weight, based on the total weight of the supported catalyst.

In addition to palladium and/or its compounds, gold and/or its compounds can additionally also be present. A particularly suitable gold compound is barium acetoaurate. In general, gold or one of its compounds, if it is employed, is added in an amount of 0.2 to 0.7% by weight, relative to the total weight of the supported catalyst, only the gold component being calculated in the case of a gold compound.

The catalyst contains alkali metal compounds and, if appropriate, additionally cadmium compounds as activators. Suitable compounds are, for example, alkali metal carboxylates such as, for example, potassium acetate, sodium acetate, lithium acetate and sodium propionate. Suitable alkali metal compounds are also those which change into the carboxylates under the reaction conditions, such as, for example, hydroxides, oxides and carbonates. Suitable compounds of cadmium are those which contain no halogen or sulfur, for example the carboxylate (preferred), oxide, hydroxide, carbonate, citrate, tartrate, nitrate, acetylacetonate, benzoylacetonate and acetoacetate. Cadmium acetate is particularly suitable. Mixtures of various activators can also be employed. Each individual activator is in general added in an amount of 0.5-4% by weight, only the metal component of the activator being calculated, in particular relative to the total weight of the supported catalyst.

The following catalysts are preferred:
palladium/cadmium/alkali metal element and palladium/gold/alkali metal element, it being possible for palladium or gold to be present as metals or as compounds in the finished catalyst and potassium being preferred as the alkali metal element (in the form of a carboxylate). The ratio K:Pd or K:(Pd+Au) is in this case preferably 0.7:1 to 2:1. The ratio Cd:Pd or Cd:(Pd+Au) is preferably 0.6:1 to 2:1, in particular 0.6:1 to 0.9:1. In this case, Pd, Au, Cd and K are always calculated as elements, i.e., for example, only the metal components of Pd acetate, Cd acetate and K acetate on the support are compared with one another.

The catalysts palladium acetate/cadmium acetate/potassium acetate and palladium acetate/barium acetoaurate/potassium acetate are particularly preferred.

The impregnation of the catalyst support with the solution of the active components is preferably carried out in such a way that the support material is covered with the solution and the excess solution is then poured off or filtered off. With regard to solution losses, it is advantageous to employ only the solution corresponding to the integral pore volume of the catalyst and to mix carefully so that the particles of the support material are uniformly wetted. This thorough mixing can be achieved, for example, by stirring. It is expedient to carry out the impregnation process and the thorough mixing at the same time, for example in a rotating drum or a tumble dryer, it being possible for the drying to follow immediately. It is furthermore expedient to measure the amount and the composition of the solution used for impregnating the catalyst support such that it corresponds to the pore volume of the support material and that the desired amount of active substances is applied by impregnating only once.

The catalyst support impregnated with the solution of the active substances is preferably dried under reduced pressure. The temperature during the drying should be below 120° C., preferably below 90° C. It is furthermore in general recommended to carry out the drying in a stream of inert gas, for example in a stream of nitrogen or carbon dioxide. The residual solvent content after drying should preferably be less than 8% by weight, in particular less than 6% by weight.

If reduction of the palladium compounds (and if desired of the gold compounds) is carried out, which may sometimes be useful, this can be carried out in vacuo, at normal pressure or at elevated pressure up to 10 bar. In this case it is recommended to dilute the reductant all the more strongly with an inert gas, the higher the pressure. The reduction temperature is between 40° and 260° C., preferably between 70° and 200° C. In general, it is expedient to use an inert gas/reductant mixture which contains 0.01 to 50 vol.-%, preferably 0.5 to 20 vol.-% reductant, for the reduction. Nitrogen, carbon dioxide or a rare gas, for example, can be used as the inert gas. Suitable reductants are, for example, hydrogen, methanol, formaldehyde, ethylene, propylene, isobutylene, butylene and other olefins. The amount of the reductant depends on the amount of palladium and, if appropriate, of gold employed; the reduction equivalent should be at least 1 to 1.5 times the oxidation equivalent, but larger amounts of reductant are not harmful. For example, at least 1 mol of hydrogen should be used relative to 1 mol of palladium. The reduction can be carried out in the same unit following the drying.

The vinyl acetate is in general prepared by passing acetic acid, ethylene and oxygen or oxygen-containing gases at temperatures of 100° to 220° C., preferably 120° to 200° C., and at pressures of 1 to 25 bar, preferably 1 to 20 bar, over the finished catalyst, it being possible to circulate unreacted components. The oxygen concentration is expediently kept below 10 vol.-% relative to the acetic acid-free gas mixture). Under certain circumstances, however, dilution with inert gases such as nitrogen or carbon dioxide is also advantageous. $CO_2$ is particularly suitable for dilution in circulation processes, since it is formed in small amounts during the reaction.

The following examples are intended to illustrate the invention.

COMPARISON EXAMPLE 1

(Spherical support particles of conventional silica gel)

200 g of a binder-free silicic acid support which consisted of annealed (800° C.) silica gel spheres of 5-8 mm diameter were employed. The (commercial) support formed from these spherical particles had a BET surface area of 169 $m^2/g$ and a pore volume of 0.48 ml/g, which was composed to 8% of pores having 70-100 Å diameter and to 29% of pores having 200-3000 Å diameter. The support was impregnated with a solution (corresponding to this pore volume) of 11.5 g of Pd acetate, 10.0 g of Cd acetate and 10.8 g of K acetate in 66 ml of glacial acetic acid and dried at 60° C. under nitrogen at a pressure of 200 mbar to a residual solvent content of 2% by weight. This gave a doping of 2.3% by weight of Pd, 1.8% by weight of Cd and 2.0% by weight of K (Cd:Pd =0.78:1, K:Pd=0.87:1).

50 ml of the finished catalyst were packed into a reaction tube of 8 mm internal diameter and of a length of 1.5 m. The gas to be reacted was then passed over the catalyst at a pressure of 8 bar (reactor inlet) and a catalyst temperature of 150° C. This gas consisted at the reactor inlet of 27 vol.-% of ethylene, 55 vol.-% of $N_2$, 12 vol.-% of acetic acid and 6 vol.-% of $O_2$. The results can be seen from the table.

COMPARISON EXAMPLE 2

(Spherical support particles of conventional $SiO_2$)

200 g of a silicic acid support were employed which had been compressed without binder from bentonite which had been calcined and then washed with HCl (96% by weight $SiO_2$ content after this wash) to give spheres of 5-6 mm diameter. The support made of these spherical particles had a BET surface area of 121 $m^2/g$ and a pore volume of 0.66 ml/g, which was composed to 21% of pores having 70-100 Å diameter and to 42% of pores having 200-3000 Å diameter. The support particles were impregnated as in Comparison Example 1 (except that 114 ml of glacial acetic acid were used instead of 66 ml) and dried so that the same doping was present as in that case. The catalyst was then tested as in Comparison Example 1. The results can be seen from the table.

COMPARISON EXAMPLE 3

A support was first prepared from $SiO_2$ microspheres having a surface area of 200 $m^2/g$ and also microcrystalline cellulose as a filler, graphite as a lubricant and kaolin as a binder. The finished support had a pore volume of 0.80 ml/g, which was composed to 62% of pores having 70-100 Å diameter and to 9% of pores having 200-3000 Å diameter. The support particles had the shape of cylinders having curved end surfaces (6 mm diameter and 6 mm height; the shape is similar to the shape of the known pharmaceutical capsules). The surface area of the support particles was 185 $m^2/g$.

The support particles (200 g) were impregnated as in Comparison Example 1 (except that 141 ml of glacial acetic acid were used instead of 66 ml) and dried so that the same doping was present as in that case. The catalyst was then tested as in Comparison Example 1. The results can be seen from the table.

COMPARISON EXAMPLE 4

A support was first prepared from $SiO_2$-$Al_2O_3$ microspheres (97% by weight of $SiO_2$, 3% by weight of $Al_2O_3$) having a surface area of 170 $m^2/g$ and sugar as a filler, graphite as a lubricant and kaolin as a binder. The finished support had a pore volume of 0.75 ml/g, which was composed to 58% of pores having 70-100 Å diameter and to 12% of pores having 200-3000 Å diameter. The support particles had the same form and size as in Comparison Example 3, but they now had a surface area of 132 $m^2/g$. The support particles (200 g) were impregnated as in Comparison Example 1 (except that 131 ml of glacial acetic acid were used instead of 66 ml) and dried so that the same doping was present as in that case. The catalyst was then tested as in Comparison Example 1. The results can be seen from the table.

EXAMPLE 1

The support was prepared as in Comparison Example 3, except that about 10% by weight of Mg stearate was used as a binder; the finished support contained 0.4% by weight of Mg. It had a surface area of 186 $m^2/g$ and a pore volume of 0.8 ml/g, 78% of the pore volume being formed of pores having radii of 70-100 Å and 16% of the pore volume of pores having radii of 200-3000 Å. The support particles had the same form and size as in Comparison Example 3 and 4.

The support particles (200 g) were impregnated as in Comparison Example 1 (except that because of the higher pore volume 141 ml of glacial acetic acid were used instead of 66 ml) and dried so that the same doping was present as in that case. The catalyst was then tested as in Comparison Example 1. The results can be seen from the table.

EXAMPLE 2

The support was prepared as in Example 1, except that 10% by weight of Al stearate were now employed instead of Mg stearate; the finished support contained 0.3% by weight of Al. It had a surface area of 164 m²/g and a pore volume of 0.91 ml/g, 76% of the pore volume being formed of pores having radii of 70–100 Å and 18% of the pore volume of pores having radii of 200–3000 Å. The support particles had the same shape and size as in Example 1 and Comparison Examples 3 and 4.

The support particles (200 g) were impregnated as in Comparison Example 1 (except that because of the higher pore volume 160 ml of glacial acetic acid were used instead of 66 ml) and dried so that the same doping was present as in that case. The catalyst was then tested as in Comparison Example 1. The results can be seen from the table.

TABLE

| | Comparison Example 1 | Comparison Example 2 | Comparison Example 3 | Comparison Example 4 | Example 1 | Example 2 |
|---|---|---|---|---|---|---|
| STY (g/l · h) | 440 | 742 | 773 | 763 | 838 | 790 |
| Combustion (%) | 14 | 15 | 6 | 8 | 5.4 | 4.6 |
| Ethyl acetate content (ppm) | 260 | 280 | 160 | 184 | 190 | 218 |

"STY" is the space-time yield; "Combustion (%)" is the percentage of reacted ethylene which is converted to $CO_2$. "Ethyl acetate content" relates to the ethyl acetate content of the condensed part of the reaction product.

We claim:

1. A method for making a catalyst which contains palladium and/or its compounds and optionally gold and/or compounds and which contains as activators alkali metal compounds and optionally cadmium compounds on a support which is comprised of $SiO_2$ or an $SiO_2$-$Al_2O_3$ mixture having a surface area of 50–250 m²/g and a pore volume of 0.4–1.2 ml/g and whose particles have a particle size of 4 to 9 mm, 5 to 20% of the pore volume of the support being formed of pores having radii of 200 to 3000 Å and 50 to 90% of the pore volume being formed of pores having radii of 70 to 100 Å, which comprises compressing the support particles with the aid of Mg or Al salt of a $C_2$–$C_{20}$ carboxylic acid or a mixture of such salts as binder, thereby obtaining a finished support with said surface area, pore volume, and particle size, calcining in $O_2$ containing gases and applying palladium and/or its compound and an alkali metal compound to the finished support.

2. The method as claimed in claim 1, wherein Mg carboxylates are employed as binders.

3. The method as claimed in claim 1, wherein said Mg or Al salt or salts are employed such that the sum of the amounts of Mg and Al calculated as elements is 0.1 to 5% by weight.

4. The method as claimed in claim 1, wherein said Mg or Al salt or salts are employed such that the sum of the amounts of Mg and Al calculated as elements is 0.3 to 1.5% by weight.

5. The method as claimed in claim 1, wherein carboxylic acid has 12 to 18 carbon atoms.

6. The method as claimed in claim 1, wherein the surface area is 150–250 m2/g.

7. The method as claimed in claim 1, wherein the $SiO_2$-$Al_2O_3$ is comprised of at least 95% by weight of $SiO_2$ and at most 5% by weight of $Al_2O_3$.

8. The method as claimed in claim 7, wherein there is at least 99% by weight of $SiO_2$ at at most 1% by weight $Al_2O_3$.

9. The method as claimed in claim 1, wherein the content of palladium is 1–3% b y weight based on the total weight of the supported catalyst.

10. The process as claimed in claim 9, wherein the content of palladium in the catalyst is 1.5–2.5% by weight based on the total weight of the supported catalyst.

11. The method as claimed in claim 1, wherein gold and/or its compounds is present.

12. The method as claimed in claim 11, wherein gold and/or its compounds is added in an amount of 0.2 to 0.7% by weight relative to the total weight of the support catalyst, only the gold component being calculated in the case of the gold compound.

13. The process as claimed in claim 12, wherein the gold compound is barium acetoaurate.

14. The method as claimed in claim 1, further comprising cadmium compound are additionally used as an activator.

15. The method as claimed in claim 14, wherein cadmium acetate is used as the cadmium compounds.

16. The method as claimed in claim 14, wherein there are mixtures of various activators.

17. The method as claimed in claim 16, wherein each individual activator is added in an amount of 0.5–4% by weight, only the metal component of each activator being calculated relative to the total weight of the support catalyst.

18. The method as claimed in claim 1, wherein the catalyst is palladium/cadmium/alkali metal element or palladium/gold/alkali metal element.

19. The method as claimed in claim 1, wherein the ratio of cadmium:palladium or cadmium:(palladium+gold) is from 0.6:1 to 2.1.

20. The method as claimed in claim 1, wherein the ratio of cadmium:palladium or cadmium:(palladium+gold) is from 0.6:1 to 0.9:1.

* * * * *